United States Patent [19]
Wada et al.

[11] Patent Number: 5,929,275
[45] Date of Patent: Jul. 27, 1999

[54] CATALYST AND PROCESS FOR PRODUCING UNSATURATED ALDEHYDE AND UNSATURATED ACID

[75] Inventors: Koichi Wada, Kanagawa-ken; Akira Iwamoto; Yoshimasa Seo, both of Yamaguchi-ken; Atsusi Sudo, Gunma-ken; Fumio Sakai, Gunma-ken; Kazuo Shiraishi, Gunma-ken; Hideaki Miki, Yamaguchi-ken, all of Japan

[73] Assignee: Nippon Kayaku Co., Ltd., Tokyo, Japan

[21] Appl. No.: 08/853,215

[22] Filed: May 9, 1997

[30] Foreign Application Priority Data

May 14, 1996 [JP] Japan ..................................... 8-142329
Mar. 19, 1997 [JP] Japan ..................................... 9-084627

[51] Int. Cl.$^6$ ......................... C07C 51/16; C07C 45/32; B01J 23/16
[52] U.S. Cl. ......................... 562/545; 562/546; 562/547; 562/538; 568/477; 568/479; 502/306; 502/308; 502/311; 502/313; 502/317
[58] Field of Search .................................... 562/538, 545, 562/547, 546; 502/306, 308, 311, 313, 317; 568/477, 479

[56] References Cited

U.S. PATENT DOCUMENTS

| | | | |
|---|---|---|---|
| 4,276,196 | 6/1981 | Dalton et al. | 252/435 |
| 4,479,013 | 10/1984 | Khoobiar | 568/479 |
| 5,221,653 | 6/1993 | Jaeger et al. | 502/212 |

FOREIGN PATENT DOCUMENTS

| | | |
|---|---|---|
| 0 493 275 | 7/1992 | European Pat. Off. . |
| 29 43 704 | 5/1980 | Germany . |
| 29 43 707 | 5/1980 | Germany . |

*Primary Examiner*—Samuel Barts
*Assistant Examiner*—Rosalynd Keys
*Attorney, Agent, or Firm*—Nields, Lemack & Dingman

[57] ABSTRACT

A catalyst for the production of unsaturated aldehyde and unsaturated acid, obtained by loading a catalytically active component on a carrier and calcining the loaded catalyst, characterized by an average particle diameter of the catalyst of 4 to 16 mm, an average particle diameter of the carrier of 3 to 12 mm, a calcining temperature of 520 to 600° C. and an amount of the catalytically active component loaded on the carrier of 5 to 80% by weight [weight of the catalytically active component)/(weight of the catalytically active component+weight of the carrier+weight of a strength improver)], and a process for producing unsaturated aldehyde and unsaturated acid with the catalyst.

4 Claims, No Drawings

CATALYST AND PROCESS FOR PRODUCING UNSATURATED ALDEHYDE AND UNSATURATED ACID

FIELD OF INDUSTRIAL APPLICATION

The present invention relates to a process for producing unsaturated aldehyde and unsaturated acid and a catalyst used therefor.

PRIOR ART

Various hybrid oxide catalyst containing molybdenum, bismuth and iron and used for the catalytic oxidation of an olefin having 3 or 4 carbon atoms in a gas phase to form the corresponding unsaturated aldehyde and unsaturated acid were already proposed, and some of them are used on an industrial scale. These catalysts are typified by, for example, those described in Japanese Patent Publication Nos. 27490/1972, 42241/1972, 1645/1973 and 61011/1982 etc.

However, various problems are posed in the production of unsaturated aldehyde or both unsaturated aldehyde and unsaturated acid on an industrial scale in the presence of such a catalyst.

One of the problems is that local, abnormally heated portions (hot spots) are formed in the catalyst layer. The hot spots are formed because the gas-phase catalytic reaction is an exothermic reaction. To improve the productivity in the production of unsaturated aldehyde and unsaturated acid on an industrial scale, it is a usual practice to increase the concentration of the starting olefin or to increased the space velocity.

However, under such high load reaction condition, an increase in the heat buildup in the hot spots causes shortening of the catalyst life, excess oxidation reaction and, in the worst case, runaway of the reaction.

Although it is a common practice to content oneself with a low productivity or to take countermeasures such as reduction in the diameter of the reaction tube against the formation of hot spots or abnormal heat buildup in the hot spots, it cannot but be said that they are economically disadvantageous.

Various investigations have been made and reported for securing an economical production on an industrial scale while avoiding the dangers caused by the hot spots in the reaction operation. Methods proposed hitherto include, for example, a method wherein a substance inert to hot spot-forming catalysts is mixed in the catalyst to dilute it (Japanese Patent Laid-Open No. 10614/1972) and a method wherein the catalyst used is tubular (Japanese Patent Publication No. 36739/1987). In addition, the following methods have also been proposed: a method wherein two reaction zones are formed in a reaction tube (Japanese Patent Laid-Open No. 127013/1976, a method wherein, in the oxidation of propylene, two or more kinds of catalysts having activities different from each other, which are produced by varying the composition (particularly the kind and/or amount of the alkaline metal), are fed into a reaction tube along its axis so that the activities of the catalysts are gradually increased in the direction from the inlet for the starting gas toward the outlet (Japanese Patent Publication No. 38331/1988), and a method wherein catalysts having different space occupation are fed into a reaction tube so that the occupied space is gradually reduced in the direction from the inlet side toward the outlet side of the reaction tube to form two or more reaction zones along the axis of the reaction tube (Japanese Patent Laid-Open No. 217932/1992).

However, in the method wherein the catalyst is diluted with an inert substance, the time taken for charging the catalyst into a reactor is increased in the periodic maintenance of plants, since the inert substance used for the dilution is to be homogeneously mixed with the catalyst before the charging. In addition, since the homogeneous mixing is not always possible in this method, heat buildup is rather increased in the hot spots in the portions of a high catalyst concentration. Another disadvantage of this method is that the hot spots are different from each other in the position and temperature in each reaction tube, which is inconvenient for the reaction operation. Thus, this method is unsatisfactory for controlling the increase in the heat buildup in the hot spots.

The method wherein an tubular catalyst is used to control the catalytic activity is also insufficient for controlling the hot spot formation under high-load reaction conditions including a high concentration of the starting material and a high space velocity.

The method wherein the catalytic activity is controlled by changing the kind and/or amount of the alkaline metal has a defect that since the amount of the alkaline metal used is far smaller than that of other components, the increase or decrease of the catalytic activity by the addition thereof is so large as to make the operation in the preparation of the catalyst very difficult. In addition, the control of the catalytic activity becomes more difficult by the effects of the alkali metal contained in the starting material for other components which are used in large amounts.

In the method wherein catalysts having different space occupation are fed into the reaction tube so that the occupied space is gradually reduced in the direction from the inlet side toward the outlet side of the reaction tube to form two or more reaction zones along the axis of the reaction tube, an extremely complicated operation is necessary for charging the catalyst, and the time taken for charging the catalyst is increased in the periodic maintenance of the plant. This is very disadvantageous from the viewpoint of the economization in the operation of the plant on an industrial scale.

PROBLEM TO BE SOLVED BY THE INVENTION

An object of the present invention is to provide a process for efficiently producing unsaturated aldehyde and unsaturated acid by solving the above-described problems of the prior art, and also to provide a catalyst suitable for the process.

More specifically, the object of the present invention is to provide a process for producing unsaturated aldehyde and unsaturated acid by the gas-phase catalytic oxidation of an olefin or tertiary alcohol under highly loaded reaction conditions, wherein the heat buildup in the hot spots in the catalyst layer is controlled without necessitating any complicated feeding operation as necessitated in the prior art to obtain a high yield of the intended product, and a stable production can be continued for a long period of time by preventing the catalyst from undergoing deterioration caused by heat load.

MEANS FOR SOLVING THE PROBLEM

In exothermic reactions like the above-described gas-phase catalytic oxidation reaction, catalytically active components have been shaped in various ways in the prior art and the shaped articles mainly comprise catalytically active components. Supposing that the catalyst is the site for the gas-phase catalytic oxidation reaction, heat generation occurs exactly on the catalyst. Accordingly, when the shaped catalyst is used for the reaction, the heat generated by the reaction concentrates thereon induce the formation of hot spots. After intensive investigations made for the purpose of reducing the apparent density of the catalytically active component to avoid the concentration of the heat of reaction generated on the catalyst, the inventors have found that the purpose can be attained by controlling the amount of the catalytically active component to be loaded on an inactive carrier, the particle size of the catalyst and the calcining temperature. The present invention has been completed on the basis of this finding.

Accordingly, the present invention relates to a catalyst obtained by loading a catalytically active component on a carrier and then calcining the loaded catalyst, characterized by a particle diameter of the catalyst of 4 to 16 mm, an average particle diameter of the carrier of 3 to 12 mm, a calcining temperature of 500 to 600° C. and an amount of the catalytically active component loaded on the carrier of 5 to 80% by weight [(weight of the catalytically active component)/(weight of the catalytically active component+weight of the carrier+weight of a strength improver)]. The catalyst of the present invention is preferably an oxidation catalyst.

The catalyst of the present invention, wherein the catalytically active component preferable has a composition represented by the following formula (1):

$$Mo_aBi_bNi_cCo_dFe_fY_gZ_hO_x \quad (1)$$

wherein Y represents at least one element selected from among tin, zinc, tungsten, chromium, manganese, magnesium, antimony and titanium; Z represents at least one element selected from among potassium, rubidium, thallium and cesium;

and a, b, c, d, f, g, h and x represent the numbers of atoms of molybdenum, bismuth, nickel, cobalt, iron, Y, Z and oxygen, respectively, provided a=12, b=0.1 to 7, preferably b=0.5 to 4, c+d=0.5 to 20, preferably c+d=1 to 12, f=0.5 to 8, preferably f=0.5 to 5, g=0 to 2, preferably g=0 to 1, h=0 to 1, preferably h=0.01 to 0.5, and x is a value which varies depending on the degrees of the oxidation of metal components.

And also, the present invention relates to a process for producing unsaturated aldehyde and unsaturated acid by the gas-phase catalytic oxidation of at least one compound selected from among propylene, isobutylene and t-butanol with molecular oxygen or a molecular oxygen-containing gas to form the corresponding unsaturated aldehyde and unsaturated acid, characterized by using the catalyst described above.

(4) the process described in the above item (3), characterized in that the catalyst described in the above item (1) or (2) is fed into each reaction tube in a multitubular reactor of fixed bed type to form one layer.

MODE FOR CARRYING OUT THE INVENTION

Now, a detailed description on the present invention will be made.

The catalyst of the present invention can be obtained by loading a catalytically active component on a carrier and calcining them. The kind of the metal element constituting the catalytically active component used for obtaining the catalyst of the present invention is not particularly limited so far as the metal element is the same as that used as the catalytically active component of a catalyst usually used for the gas phase catalytic oxidation reaction of olefin or tertiary alcohol. Among such catalysts, the one represented by the formula (1) in the above item (2) is preferred.

The catalytically active component is usually prepared by the methods known per se, such as the coprecipitation method, and the starting materials used in the method, which are not particularly limited, are, for example, nitrates, ammonium salts, hydroxides, etc., of the metal elements constituting the catalytically active component. The catalytically active component is usually calcined at 200 to 600° C. for 2 to 7 hours before being loaded on the carrier to form a pre-calcined powder. The pre-calcining is conducted preferably in air or nitrogen stream.

In loading the pre-calcined powder on the carrier, a molding aid and/or a strength improver is preferably used. Examples of the molding aids usable herein include crystalline cellulose, starch and stearic acid. The molding aid is used usually in an amount of 30% by weight or less based on the pre-calcined powder. Examples of the strength improvers usable herein include ceramic fibers, carbon fibers and whiskers. The strength improver is used usually in an amount of 30% by weight or below based on the pre-calcined powder. The molding aid and/or strength improver may be mixed with the pre-calcined powder prior to loading the catalyst on the carrier or when, before or after the pre-calcined powder and other materials are fed into a molding machine as will be described before.

In loading the pre-calcined powder on the carrier, also a binder is preferably used. Examples of the binders usable herein include water, high-molecular binders such as polyvinyl alcohols, inorganic binders such as silica sol and alumina sol, polyhydric alcohols such as ethylene glycol and glycerol, and mixtures of them.

The binder is used in an amount of usually 10 to 60% based on the pre-calcined powder.

The shape of the carrier is not particularly limited and the carrier may be, for example, spherical, cylindrical or tubular. From the viewpoints of the production efficiency and the mechanical strength of the catalyst, the spherical shape is preferred. The average particle diameter of the carrier which is suitably determined depending on the inner diameter of the reaction tube in which the catalyst is to be fed and the amount of the catalytically active component-containing powder to be carried is usually 3 to 12 mm, preferably 3.5 to 9 mm more preferably 3.7 to 7 mm.

Any carrier which is catalytically inactive and porous or which can be shaped into porous particles is available. Examples of the materials usable as the carrier include a-alumina, silicon carbide, pumice, silica, zirconium oxide and titanium oxide.

The catalytically active component can be loaded on the carrier by any method capable of uniformly loading the component on the carrier such as the tumbling granulation method, the method wherein a centrifugal fluidization coater is used or the wash coating method. From the viewpoint of the production efficiency of the catalyst, the tumbling granulation method is preferred. In particular, in this preferred method, an apparatus having a disc having a smooth or rough surface at the bottom of a fixed cylindrical vessel is used, and the disc is rotated at such a high speed that the carrier charged in the vessel is violently stirred by the rotation of the carrier itself and also by the revolution. The catalytically active component and, if necessary, the binder, molding aid and strength improver are added thereto to load the powder components on the carrier. The amount of the catalytically active component which varies depending on the operation conditions such as the inner diameter of the reaction tube is usually 5 to 80% by weight, preferably 10 to 60% by weight more preferably 30 to 50% by weight [weight of the catalytically active component/(weight of the catalytically active component+weight of the carrier+weight of the strength improver (optional component))] (hereinafter referred to as the catalyst-loading rate). The term "weight of the catalytically active component" refers to the weight of the pre-calcined powder. By the tumbling granulation method which is a preferred mode for producing the catalyst of the present invention, almost 100% of the predetermined amount of the pre-calcined powder (or the powder further containing the molding aid and/or strength improver) can be loaded.

Then the catalytically active component loaded on the carrier is calcined to obtain the catalyst of the present invention. The calcining temperature which varies depending on the operation conditions such as the inner diameter of the reaction tube is usually 500 to 600° C., preferably 520 to 560° C. The calcining time is usually 3 to 30 hours, preferably 4 to 15 hours. The particle size of the catalyst which varies depending on the inner diameter of the reaction tube, the average particle size of the carrier and the catalyst-loading rate is usually 4 to 16 mm, preferably 4 to 10 mm, more preferably 4 to 7 mm. The particle size of the catalyst after the calcining is substantially equal to that before the calcining.

Next, a detailed description will be made on the production process of the present invention.

In the production process of the present invention wherein a multitubular reactor of fixed bed type is usually used, the length of the filled catalyst, the inner diameter of the reaction tube and the number of the tubes vary depending on the operation conditions. Therefore, the catalyst-loading rate, the calcining temperature and the particle size of the catalyst are suitably determined depending thereon so as to obtain an optimum yield. For example, when the inner diameter of the reaction tube is 21 to 28 mm, then the catalyst-loading rate is preferably 20 to 50% by weight, the catalyst particle size is preferably 4 to 8 mm and the calcining temperature is preferably 500 to 580° C.

The catalyst of the present invention is used preferably for the gas-phase catalytic oxidation of olefin or tertiary alcohol to produce the corresponding unsaturated aldehyde and unsaturated acid, and still preferably for producing acrolein and acrylic acid or methacrolein and methacrylic acid from propylene, isobutylene or t-butanol.

The gas-phase catalytic oxidation reaction in the present invention may be carried out by an ordinary single pass method or the recycle method, the reaction can be carried out under the conditions usually employed for a reaction of this kind except that the catalyst of the present invention is used. In using the catalyst of the present invention charged in the reaction tube, it is preferred to form one layer (one-layer charging). The one-layer charging is preferred particularly when acrolein is produced from propylene.

When, for example, at least one compound selected from among propylene, isobutylene and t-butanol is used as the starting material, the process of the present invention is conducted by introducing a mixed gas comprising 1 to 10% by volume, preferably 4 to 9% by volume, of the starting material, 3 to 20% by volume, preferably 4 to 18% by volume, of molecular oxygen, 0 to 60% by volume, preferably 4 to 50% by volume, of water vapor, 20 to 80% by volume, preferably 30 to 60% by volume, of an inert gas (such as nitrogen or carbon dioxide etc.) into a reaction tube filled with the catalyst of the present invention at a space velocity (=flow rate of the starting gas/apparent volume of the charged catalyst) of 300 to 5,000 hour$^{-1}$, preferably 800 to 2,000 hour$^{-1}$ at a temperature of 250 to 450° C. under a pressure of atmospheric pressure to 10 atm.

EFFECT OF THE INVENTION

The following effects are obtained by conducting the oxidation reaction of olefin or the like in the presence of the catalyst of the present invention charged to form one layer:

(a) the temperature of the hot spots can be kept low to avoid the danger of the runaway of the reaction caused by the abnormal temperature rise.

(b) the excessive oxidation reaction in the hot spots can be prevented to obtain high yields of the intended unsaturated aldehyde and unsaturated acid and also high selectivities toward them, (c) the catalyst can be prevented from suffering deterioration by the heat load, and the catalyst can be used stably for a long period of time, (d) since the intended unsaturated aldehyde and unsaturated acid can be produced under high-load reaction conditions such as a high concentration of the starting material and a high space velocity, the productivity can be remarkably improved.

(e) the pressure loss in the catalyst layer can be kept low, and (f) since multi-layer charging is unnecessary, the time taken for charging the catalyst in the periodic maintenance of the plant can be remarkably reduced.

Thus, the catalyst and process of the present invention are very useful for the production of unsaturated aldehyde and unsaturated acid.

EXAMPLES

The following Examples will further illustrate the present invention.

In the Examples, the conversion, selectivity and one-pass yield are defined as follows:

conversion (molar %)=(molar number of reacted starting material)/(molar number of fed starting material)×100 selectivity (molar %)=(molar number of formed unsaturated aldehyde or unsaturated acid)/(molar number of reacted starting material)×100 yield (molar %)=(molar number of formed unsaturated aldehyde or unsaturated acid)/(molar number of fed starting material)×100

Example 1

Preparation of Catalyst 423.8 g of ammonium molybdate and 2.02 g of potassium nitrate were dissolved in 3,000 ml of distilled water under stirring and heating to obtain an aqueous solution (A). Separately, 302.7 g of cobalt nitrate, 162.9 g of nickel nitrate and 145.4 g of ferric nitrate were dissolved in 1,000 ml of distilled water to obtain an aqueous solution (B). 164.9 g of bismuth nitrate was dissolved in 200 ml of distilled water acidified with 25 ml of concentrated nitric acid to obtain an aqueous solution (C). The aqueous solutions (B) and (C) were mixed together, and the obtained solution was dropped into the aqueous solution (A) under vigorous stirring.

The suspension thus obtained was dried with a spray dryer and then pre-calcined at 440° C. for 3 h to obtain 570 g of the pre-calcined powder. 200 g of this powder was mixed with 10 g of crystalline cellulose as the molding aid.

300 g of an alumina carrier having an average particle size of 4 mm was fed into a tumbling granulator. Then the mixture obtained above and 90 g of 33% aqueous glycerol solution as the binder were added thereto at the same time to load the mixture on the carrier and thereby to obtain the particles (hereinafter referred to as the "active component-loading particles") having a catalyst-loading rate of 40% by weight.

The active component-loading particles were dried at room temperature for 15 h and then calcined at 520° C. for 5 h in an air stream to obtain a catalyst (1) of the present invention. The catalyst thus obtained had an average particle size of 4.5 mm, and the atomic ratio of the catalytically active components, excluding oxygen, was as follows: Mo=12:Bi=1.7:Ni=2.8:Fe=1.8:Co=5.2:K=0.1.

Oxidation Reaction 1,300 ml of the catalyst (1) prepared above was fed into a stainless steel (SUS 304) reaction tube having an average inner diameter of 21 mm and provided with a jacket for circulating a molten salt as the heat transfer medium and a thermocouple for determining the catalyst layer temperature on the shaft thereof. A mixed gas comprising 8% by volume of propylene, 14% by volume of oxygen, 25% by volume of water vapor and 53% by volume of nitrogen was introduced into the tube at a space velocity of 1,300 h$^{-1}$ while keeping the molten salt temperature at 334° C. to conduct the reaction. In the course of the reaction, the temperature of the hot spots (spots of the highest reaction temperature) was 416° C., the conversion of propylene was 97.2%, the yield of acrolein was 80.3%, the yield of acrylic acid was 9.9%, and the total selectivity toward acrolein and acrylic acid was 92.8%. Even after continuing the reaction for 1,000 h or longer, no worsening of the reaction was found.

Example 2

The reaction was conducted in the same manner as that of Example 1 except that the calcining temperature of the active component-loading particles was altered to 540° C. [catalyst (2)], that this catalyst was used and that the molten salt temperature was altered to 365° C. The temperature of the hot spots was 424° C., the conversion of propylene was 98.4%, the yield of acrolein was 80.4%, the yield of acrylic acid was 10.4%, and the total selectivity toward acrolein and acrylic acid was 92.3%. Even after continuing the reaction for 1,000 h or longer, no worsening of the reaction results was found.

Example 3

The reaction was conducted in the same manner as that of Example 1 except that the space velocity was altered to 1,600 h$^{-1}$ and the temperature of the molten salt was altered to 349° C. The temperature of the hot spots was 457° C., the conversion of propylene was 98.0%, the yield of acrolein was 77.0%, the yield of acrylic acid was 12.9%, and the total selectivity toward acrolein and acrylic acid was 91.7%. Even after continuing the reaction for 1,000 h or longer, no worsening of the reaction results was found.

Example 4

The reaction was conducted in the same manner as that of Example 2 except that the space velocity was altered to 1,600 h$^{-1}$ and the temperature of the molten salt was altered to 360° C. The temperature of the hot spots was 415° C., the conversion of propylene was 97.1%, the yield of acrolein was 81.5%, the yield of acrylic acid was 8.9%, and the total selectivity toward acrolein and acrylic acid was 93.1%. Even after continuing the reaction for 1,000 h or longer, no worsening of the reaction results was found.

Example 5

The reaction was conducted in the same manner as that of Example 1 except that the calcining temperature of the active component-loading particles was altered to 530° C. [catalyst (3)], that the space velocity was altered to 1551 h$^{-1}$ and that the molten salt temperature was altered to 350° C. The temperature of the hot spots was 424° C., the conversion of propylene was 97.9%, the yield of acrolein was 82.3%, the yield of acrylic acid was 8.4%, and the total selectivity toward acrolein and acrylic acid was 92.6%. Even after continuing the reaction for 1,200 h, no worsening of the reaction results was found.

Example 6

The reaction was conducted in the same manner as that of Example 1 except that the average particle size of the alumina carrier was altered to 4.5 mm (the average particle size of the active component-loading particles was 5.0 mm) and that the calcining temperature, the space velocity and the temperature of the molten salt were altered to 530° C. [catalyst (4)], 1600 h$^{-1}$ and 357° C., respectively. The temperature of the hot spots was 414° C., the conversion of propylene was 97.7%, the yield of acrolein was 82.5%, the yield of acrylic acid was 8.7%, and the total selectivity toward acrolein and acrylic acid was 93.3%. Even after continuing the reaction for 1,000 h or longer, no worsening of the reaction results was found.

Example 7

The reaction was conducted in the same manner as that of Example 6 except that the calcining temperature of the active component-loading particles was altered to 540° C. [catalyst (5)] and that the molten salt temperature was altered to 362° C. The temperature of the hot spots was 443° C., the conversion of propylene was 97.7%, the yield of acrolein was 82.6%, the yield of acrylic acid was 8.8%, and the total selectivity toward acrolein and acrylic acid was 93.6%. Even after continuing the reaction for 1,000 h or longer, no worsening of the reaction results was found.

Example 8

1300 ml of the catalyst (3) prepared in Example 5 was fed into a stainless steel (SUS 304) reaction tube having an average inner diameter of 21 mm and provided with a jacket for circulating a molten salt as the heat transfer medium and a thermocouple for determining the catalyst layer temperature on the shaft thereof. A mixed gas comprising 7% by volume of propylene, 13% by volume of oxygen, 42% by volume of water vapor and 38% by volume of nitrogen was introduced into the tube at a space velocity of 1,800 h$^{-1}$ while keeping the molten salt temperature at 351° C. to conduct the reaction. In the course of the reaction, the temperature of the hot spots was 405° C., the conversion of propylene was 97.4%, the yield of acrolein was 81.7%, the yield of acrylic acid was 8.1%, and the total selectivity toward acrolein and acrylic acid was 92.2%. Even after continuing the reaction for 1,000 h or longer, no worsening of the reaction results was found.

Example 9

The reaction was conducted in the same manner as that of Example 8 except that the catalyst (4) obtained in Example 6 was used and that the temperature of the molten salt was altered to 352° C. The temperature of the hot spots was 399° C., the conversion of propylene was 97.0%, the yield of acrolein was 83.3%, the yield of acrylic acid was 7.2%, and the total selectivity toward acrolein and acrylic acid was 93.3%. Even after continuing the reaction for 1,000 h or longer, no worsening of the reaction results was found.

Example 10

The reaction was conducted in the same manner as that of Example 8 except that the catalyst (5) obtained in Example 7 was used and that the temperature of the molten salt was altered to 362° C. The temperature of the hot spots was 428° C., the conversion of propylene was 97.1%, the yield of acrolein was 82.1%, the yield of acrylic acid was 8.5%, and the total selectivity toward acrolein and acrylic acid was 93.3%. Even after continuing the reaction for 1,000 h or longer, no worsening of the reaction results was found.

Example 11

Preparation of Catalyst 423.8 g of ammonium molybdate and 2.02 g of potassium nitrate were dissolved in 3,000 ml of distilled water under stirring and heating to obtain an aqueous solution (A). Separately, 302.7 g of cobalt nitrate, 162.9 g of nickel nitrate and 145.4 g of ferric nitrate were dissolved in 1,000 ml of distilled water to obtain an aqueous solution (B). 164.9 g of bismuth nitrate was dissolved in 200 ml of distilled water acidified with 25 ml of concentrated nitric acid to obtain an aqueous solution (C). The aqueous solutions (B) and (C) were mixed together, and the obtained solution was dropped into the aqueous solution (A) under vigorous stirring.

The suspension thus obtained was dried with a spray dryer and then pre-calcined at 440° C. for 3 h to obtain 570 g of the pre-calcined powder. 200 g of this powder was mixed with 10 g of crystalline cellulose as the molding aid.

300 g of an alumina carrier having an average particle size of 5 mm was fed into a tumbling granulator. Then, 210 g of the mixture obtained above and 90 g of a 33% aqueous glycerol solution as the binder were added thereto at the same time to support the mixture on the carrier and thereby to obtain the active component-loading particles having a catalyst-loading rate of 40% by weight.

The active component-loading particles were dried at room temperature for 15 h and then calcined at 540° C. for 5 h in an air stream to obtain a catalyst (6) of the present invention. The catalyst thus obtained had an average particle size of 5.5 mm, and the atomic ratio of the catalytically active components, excluding oxygen, was as follows: Mo=12:Bi=1.7:Ni=2.8:Fe=1.8:Co=5.2:K=0.1.

Oxidation Reaction 1900 ml of the catalyst (6) prepared above was fed into a stainless steel (SUS 304) reaction tube having an average inner diameter of 27 mm and provided with a jacket for circulating a molten salt as the heat transfer medium and a thermocouple for determining the catalyst layer temperature on the shaft thereof. A mixed gas comprising 7% by volume of propylene, 13% by volume of oxygen, 30% by volume of water vapor and 50% by volume of nitrogen was introduced into the tube at a space velocity of 1500 h$^{-1}$ while keeping the molten salt temperature at 347° C. to conduct the reaction. In the course of the reaction, the temperature of the hot spots was 443° C., the conversion of propylene was 97.2%, the yield of acrolein was 84.9%, the yield of acrylic acid was 6.9%, and the total selectivity toward acrolein and acrylic acid was 94.4%. Even after continuing the reaction for 2,200 h, no worsening of the reaction results was found.

Example 12

The reaction was conducted in the same manner as that of Example 11 except that the space velocity was converted to 1,300 h$^{-1}$ and the temperature of the molten salt was altered to 346° C. The temperature of the hot spots was 453° C., the conversion of propylene was 98.1%, the yield of acrolein was 84.8%, the yield of acrylic acid was 7.4%, and the total selectivity toward acrolein and acrylic acid was 94.0%. Even after continuing the reaction for 1,000 h or longer, no worsening of the reaction results was found.

Example 13

The reaction was conducted in the same manner as that of Example 11 except that the space velocity was converted to 1,800 h$^{-1}$ and the temperature of the molten salt was altered to 349° C. The temperature of the hot spots was 444° C., the conversion of propylene was 96.7%, the yield of acrolein was 84.3%, the yield of acrylic acid was 6.9%, and the total selectivity toward acrolein and acrylic acid was 94.3%. Even after continuing the reaction for 1,000 h or longer, no worsening of the reaction results was found.

Example 14

The reaction was conducted in the same manner as that of Example 11 except that a catalyst of the present invention [catalyst (7)], obtained in the same manner as that of Example 11 except that 150 g of the pre-calcined powder, 300 g of alumina carrier having an average particle diameter of 6.0 mm and active component-loading particles having a particle diameter of 6.3 mm were used, was used and that the molten salt temperature was altered to 360° C. The temperature of the hot spots was 443° C., the conversion of propylene was 94.3%, the yield of acrolein was 84.1%, the yield of acrylic acid was 6.1%, and the total selectivity toward acrolein and acrylic acid was 95.6%. Even after continuing the reaction for 1,000 h or longer, no worsening of the reaction results was found.

Example 15

Preparation of Catalyst 450 g of ammonium molybdate and 15.3 g of cesium nitrate were dissolved in 3,000 ml of distilled water under stirring and heating to obtain an aqueous solution (A). Separately, 456 g of cobalt nitrate and 238 g of ferric nitrate were dissolved in 1,500 ml of distilled water to obtain an aqueous solution (B). 190 g of bismuth nitrate was dissolved in 200 ml of distilled water acidified with 30 ml of concentrated nitric acid to obtain an aqueous solution (C). The aqueous solutions (B) and (C) were mixed together, and the obtained solution was dropped into the aqueous solution (A) under vigorous stirring to obtain a suspension. The suspension was dried with a spray dryer and then pre-calcined at 460° C. for 5 h to obtain 580 g of the pre-calcined powder. Then 300 g of the pre-calcined powder was loaded on 300 g of an alumina carrier having an average particle size of 4 mm in the same manner as that of Example 1 to obtain the active component-loading particles having a catalyst-loading rate of 50% by weight.

The active component-loading particles were dried at room temperature for 15 h and then calcined at 520° C. for 5 h in an air stream to obtain a catalyst (8) of the present invention. The catalyst thus obtained had an average particle size of 4.4 mm, and the atomic ratio of the catalytically active components, excluding oxygen, was as follows: Mo=12:Bi=1.8:Fe=2.8:Co=7.4:Cs=0.4.

Oxidation Reaction 692 ml of the catalyst (8) prepared above was fed into a stainless steel (SUS 304) reaction tube having an average inner diameter of 21.4 mm and provided with a jacket for circulating a molten salt as the heat transfer medium and a thermocouple for determining the catalyst layer temperature on the shaft thereof. A mixed gas comprising 6% by volume of t-butanol, 13% by volume of oxygen, 3% by volume of water vapor and 78% by volume of nitrogen was introduced into the tube at a space velocity of 1200 h$^{-1}$ while keeping the molten salt temperature at 355° C. to conduct the reaction. In the course of the reaction, the temperature of the hot spots was 404° C., the conversion of t-butanol was 100%, the yield of methacrolein was 81.5%, the yield of methacrylic acid was 1.9%, and the total selectivity toward methacrolein and methacrylic acid was 83.4%. Even after continuing the reaction for 1,000 h or longer, no worsening of the reaction results was found.

Example 16

692 ml of the catalyst (8) prepared above was fed into a stainless steel (SUS 304) reaction tube having an average inner diameter of 21.4 mm and provided with a jacket for circulating a molten salt as the heat transfer medium and a thermocouple for determining the catalyst layer temperature on the shaft thereof. A mixed gas comprising 6% by volume of isobutylene, 12% by volume of oxygen, 9% by volume of water vapor and 73% by volume of nitrogen was introduced into the tube at a space velocity of 1200 h$^{-1}$ while keeping the molten salt temperature at 350° C. to conduct the reaction. In the course of the reaction, the temperature of the hot spots was 389° C., the conversion of isobutylene was 99.2%, the yield of methacrolein was 80.9%, the yield of methacrylic acid was 1.7%, and the total selectivity toward methacrolein and methacrylic acid was 83.3%. Even after continuing the reaction for 1,000 h or longer, no worsening of the reaction results was found.

We claim:

1. A catalyst for the production of unsaturated aldehyde and/or unsaturated acid, obtained by loading a catalytically active component on a carrier and calcining the loaded catalyst, characterized by an average particle diameter of the catalyst of 4 to 16 mm, an average particle size of the carrier of 3 to 12 mm, a calcining temperature of 520 to 600° C. and an amount of the catalytically active component loaded on the carrier of 5 to 80% by weight ((weight of the catalytically active component)/(weight of the catalytically active component+weight of the carrier+weight of a strength improver)).

2. The catalyst according to claim 1, wherein the catalytically active component has a composition represented by the following formula (1):

$$Mo_a Bi_b Ni_c Co_d Fe_f Y_g Z_h O_x \qquad (1)$$

wherein Y represents at least one element selected from among tin, zinc, tungsten, chromium, manganese, magnesium, antimony and titanium; Z represents at least one element selected from among potassium, rubidium, thallium and cesium; and a, b, c, d, f, g, h and x represent the numbers of atoms of molybdenum, bismuth, nickel, cobalt, iron, Y, Z and oxygen, respectively, provided a=12, b=0.1 to 7, c+d=0.5 to 20, f=0.5 to 8, g=0 to 2, h=0 to 1, and x is a value which varies depending on the degrees of the oxidation of the metal component.

3. A process for producing unsaturated aldehyde and unsaturated acid by the gas-phase catalytic oxidation of at least one compound selected from among propylene, isobutylene and t-butanol with molecular oxygen or a molecular oxygen-containing gas to form the corresponding unsaturated aldehyde and/or unsaturated acid, characterized by using the catalyst set forth in claim 1 or 2.

4. The process according to claim 3, characterized in that the catalyst set forth in claim 1 or 2 is fed into each reaction tube in a multitubular reactor of fixed bed type to form one layer.

\* \* \* \* \*